United States Patent [19]

Kajiwara et al.

[11] Patent Number: 5,762,640

[45] Date of Patent: Jun. 9, 1998

[54] EFFUSION FLUID SUCKING DEVICE

[75] Inventors: Yuji Kajiwara; Hidetaka Fujiwara, both of Tokyo, Japan

[73] Assignee: NEC Corporation, Tokyo, Japan

[21] Appl. No.: 655,938

[22] Filed: May 31, 1996

[30] Foreign Application Priority Data

May 31, 1995 [JP] Japan ................ 7-132998

[51] Int. Cl.$^6$ .................. A61M 1/00; A61B 5/00
[52] U.S. Cl. .................. 604/313; 604/289; 128/760
[58] Field of Search ................ 604/289, 312–316; 128/632, 635, 637, 760

[56] References Cited

U.S. PATENT DOCUMENTS

| 2,063,084 | 12/1936 | Farnon et al. | 604/313 |
| 4,151,832 | 5/1979 | Hamer | 604/313 |
| 4,844,097 | 7/1989 | Bellhouse et al. | 128/637 |
| 5,291,887 | 3/1994 | Stanley et al. | 604/289 |
| 5,417,206 | 5/1995 | Kaneyoshi | 128/632 |

FOREIGN PATENT DOCUMENTS 197436  4/1989  Japan.

OTHER PUBLICATIONS

"Portable Blood Glucose Monitoring System", NEC Technical Report, vol. 46, No. 9 (1993), pp. 84–91.

"Development of Biosensor Based on Semiconductor Technology", NEC Technical Report, vol. 48, No. 7 (1995).

SRL Takarabako, vol. 18, No. 3.4 (1994).

*Primary Examiner*—Robert A. Clarke
*Assistant Examiner*—David J. Cho
*Attorney, Agent, or Firm*—Sughrue, Mion, Zinn, Macpeak & Seas, PLLC

[57] ABSTRACT

A device for sucking an effusion fluid from the skin of an organism from which keratin has been removed. A disk is received in the cavity of a cell for sucking an effusion fluid in contact with the surface of an organism. Guide grooves are formed in the surface of the disk facing a suction port while holes are formed through the disk in each guide groove. The disk allows a minimum of fluid to remain thereon and guides the fluid toward the suction side in order to enhance efficient collection. When the fluid is collected a plurality of times, the preceding fluid and the following fluid are prevented from being mixed together, insuring accurate measurement.

28 Claims, 4 Drawing Sheets

5,762,640

EFFUSION FLUID SUCKING DEVICE

BACKGROUND OF THE INVENTION

The present invention relates to a device for sucking and sampling an effusion fluid from an organism and, more particularly, to an effusion fluid sucking device for collecting a small amount of humors.

The concentration of glucose, blood glucose or similar chemical substance existing in an organism has traditionally been continuously measured by sampling blood and analyzing it with an exclusive sensor. The sensor is implemented as a biosensor having an enzyme immobilized membrane electrode. Because the biosensor is small size, it can accurately measure the concentration even with a small amount of sample. This kind of method is therefore applicable to various kinds of fields including medical care, diagnosis, and biochemistry. For example, the concentration of an organic substance existing in blood, urine or the like may be measured for diagnosis by the above method. However, such a traditional method inflicts pain on the patient and needs the greatest care against infection and bleeding.

A recent achievement capable of relieving the physical pain of the patient and the mental anguish of the medical service is a method which strips the stratum corneum of a part of the skin, extracts fluid from the stripped part, and then monitor the concentration of a desired substance with a sensor. This method is disclosed in, e.g., NEC Technical Report, Vol. 46, No. 9 (1993), pp. 84–91. Specifically, an interstitial fluid sucked from the skin is brought into contact with an enzyme immobilized membrane provided on an ion sensitive field effect transistor (ISFET), so that the glucose concentration is measured in terms of the degree of reaction of the membrane. For the collection of the interstitial fluid or effusion fluid, use is made of a sucking device. For example, a conventional sucking device has a suction cell formed with a cavity. A mesh is received in the cavity and affixed to the cell by a frame. The mesh is formed of stainless steel or nylon. A chamber is evacuated via a suction port with the result that an effusion fluid is collected in the chamber.

The mesh serves to promote the smooth transfer of the effusion fluid from the cavity to the chamber. However, the fluid left on the mesh after sampling is several times as great in amount as the fluid collected in the chamber, limiting the sampling efficiency of the device.

Further, when the effusion fluid is sampled a plurality of times in order to monitor the variation in the concentration, the fluid sucked earlier left on the mesh is contaminated with the fluid sucked later. This, mixed with analyte dissolved in the fluid from the frame, prevents the concentration from being accurately measured. In addition, it is likely that the frame which is easy to deform and the end of the cavity are slightly deviated in height from each other. The resulting gap between the end of the cavity and the skin allows air to leak therethrough and thereby obstructs the evacuation, i.e., t h e suction of the fluid. Precisely flattening the end of the mesh frame which is as thin as 0.2 mm and easy to deform is extremely difficult and increases the cost, if not impossible.

Other technologies relevant to the present invention are taught in NEC Technical Report, Vo. 48, No. 7 (1995), Japanese Patent Laid-Open Publication No. 1-97436, and SRL Takarabako, Vol. 18, No. 3.4 (1994).

SUMMARY OF THE INVENTION

It is therefore an object of the present invention to provide an effusion fluid sucking device capable of collecting humors from an organism efficiently, and allowing the concentration of a desired substance existing in the humors to be measured with accuracy.

A device for sucking and collecting an effusion fluid from an organism of the present invention has a suction cell formed with a suction port for causing the effusion fluid to effuse from the organism by evacuation, and a cavity formed in the end of the suction cell for directly contacting the surface of the organism. A disk is received in the cavity for directly contacting the surface of the organism. The disk is formed with a plurality of guide grooves on its surface facing the suction port, and a plurality of through holes in each guide groove.

BRIEF DESCRIPTION OF THE DRAWINGS

The above and other objects, features and advantages of the present invention will become apparent from the following detailed description taken with the accompanying drawings in which.

DESCRIPTION OF THE PREFERRED EMBODIMENTS

Figure 1:
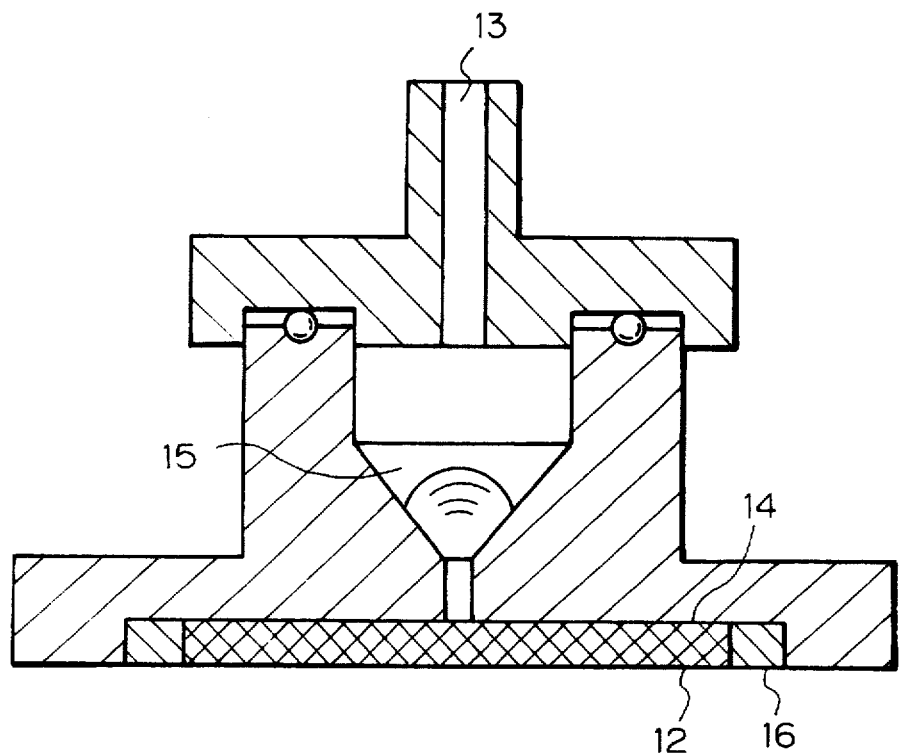
FIG. 1 is a section showing a conventional effusion fluid sucking device.

To better understand the present invention, a brief reference will be made to a conventional effusion fluid sucking device, shown in FIG. 1. As shown, the device has a suction cell for sucking an effusion fluid and formed with a cavity 14. A mesh 12 is received in the cavity 14 and affixed to the cell by a frame 16. The mesh 12 is formed of stainless steel or nylon. A chamber 15 is evacuated via a suction port 13 with the result that an effusion fluid is collected in the chamber 15. The mesh 12 serves to promote the smooth transfer of the effusion fluid from the cavity 14 to the chamber 15. However, the fluid left on the mesh 12 after sampling is several times as great in amount as the fluid collected in the chamber 15, limiting the collection efficiency of the device, as discussed earlier. Specifically, assuming that the cavity 14 has a diameter of 30 mm and a depth of 0.2 mm, then its capacity is about 50 μl. In this condition, even if the volume of the mesh 12 itself is one-third of the capacity of the cavity 14, the fluid cannot be collected in the chamber 15 unless the mesh 12 is filled with about 30 μl of fluid beforehand. Specifically, assuming that 10 μl of effusion fluid is needed, then at least 40 μl must be sucked from the skin.

Moreover, when the effusion fluid is repeatedly sampled at preselected intervals, the fluid sucked earlier is left on the mesh 12 and mixed with the fluid sucked later. This, mixed with analyte dissolved in the fluid from the frame 16, prevents the concentration from being accurately measured. In addition, it is likely that the frame 16 which is easy to deform and the end of the cavity 14 are slightly deviated in height from each other. The resulting gap between the end of the cavity 14 and the skin allows air to leak therethrough and thereby obstructs the evacuation, i.e., the suction of the fluid.

Figure 2A:
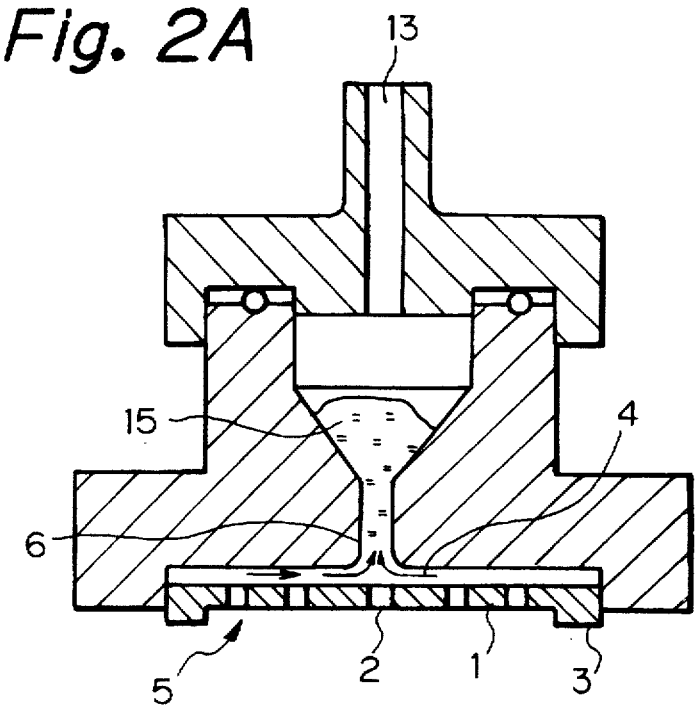
FIG. 2A and 2B are respectively a section and a bottom view showing an effusion fluid sucking device embodying the present invention.
Figure 2B:
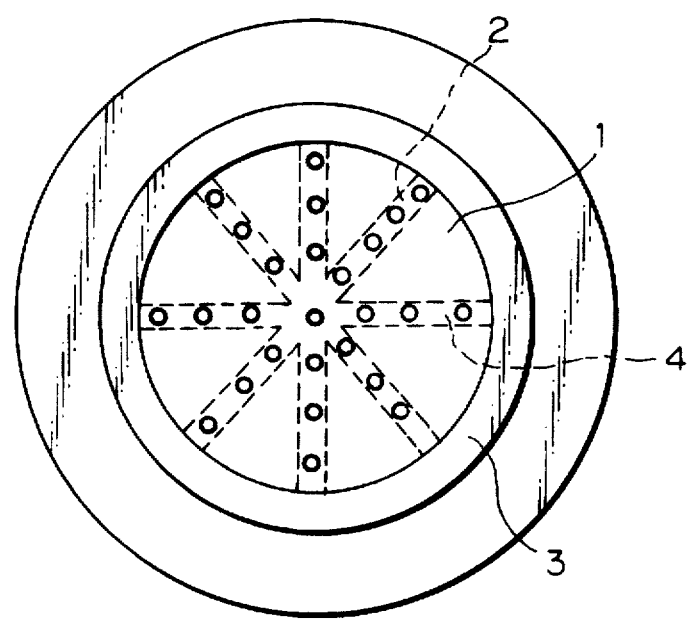

Referring to FIGS. 2A and 2B, an effusion fluid sucking device embodying the present invention will be described. As shown, the device has a suction cell formed with a cavity 5, an inlet passage 6 including guide grooves 4, a suction port 13, and a chamber 15. A disk 1 is received in the cavity 5. The guide grooves 4 are formed in the end of the disk 1 facing the suction port 13, and each extends radially outward from the center of the disk 1. A plurality of holes 2 are formed throughout the disk 1 in each guide groove 4. The disk 1 is formed of a sparingly ionizable material in order to prevent ions from being dissolved in an effusion fluid. For example, the disk 1 should preferably be made of stainless steel, nickel or similar metal or polyimide, vinyl chloride or similar polymeric material. This prevents ions dissolved in the fluid from being input to a sensor as noise when the concentration a desired substance of an interstitial fluid sampled in place of blood is measured.

The other end of the disk 1 remote from the suction port 13 should preferably be formed with an annular projection 3 along its circumferential edge, as illustrated. When the end of the cell around the cavity 5 is brought into contact with the skin, the projection 3 tightly contacts the skin and thereby enhances air-tightness. As a result, the device is free from the leak of air discussed in relation to the prior art device. The guide grooves 4 and holes 2 formed therein are sized less than 1 mm each, so that they are filled with the fluid due to capillarity. With this configuration, it is possible to exclude from the fluid air which would effect the accuracy of measurement. The grooves 4 and holes 2 should be as smooth as possible and should have such a small size. Therefore, it is preferable to form the grooves 4 and holes 2 in the disk 1 by etching using photolithography.

In operation, when the chamber 15 is evacuated through the suction port 13, an effusion fluid is sucked from the skin into the guide grooves 4 of the disk 1 via the holes 2. Then, the fluid concentratedly flows into the inlet passage 6 along the grooves 4 due to vacuum. As a result, the fluid is collected in the chamber 15, as shown in FIG. 2A, or is directly delivered to a sensor portion, not shown.

Assume that the disk 1 has a thickness of 0.1 mm and a n outside diameter of 30 mm, that the grooves 4 each has a width of 0.15 mm and a depth of 0.05 mm, and that the holes 2 each has a diameter of 0.1 mm. Then, the total capacity of the holes 2 and grooves 4 is as small as about 10 µl.

Therefore, if 10 µl of fluid is needed for measurement, then only 10 µl should be extracted from the skin. This means a remarkable improvement in the sampling efficiency over the conventional mesh scheme which requires 40 µl of fluid, as stated previously.

Assume that 10 µl of fluid is needed for measurement, as stated above, and that the measurement is repeated. Then, because the consecutive fluids forced out by capillarity are prevented from being mixed together, they can be collected in an extremely short period of time and can be measured with accuracy.

The disk 1 which is a single member remains highly rigid without resorting to a frame. Hence, the disk 1 deforms little and can be provided with precisely flat surfaces. This, coupled with the fact that the etching for forming the grooves 4 and holes 2 does not exert any pressure on the disk 1, insures higher accuracy and lower cost than the conventional mesh scheme.

Figure 3:
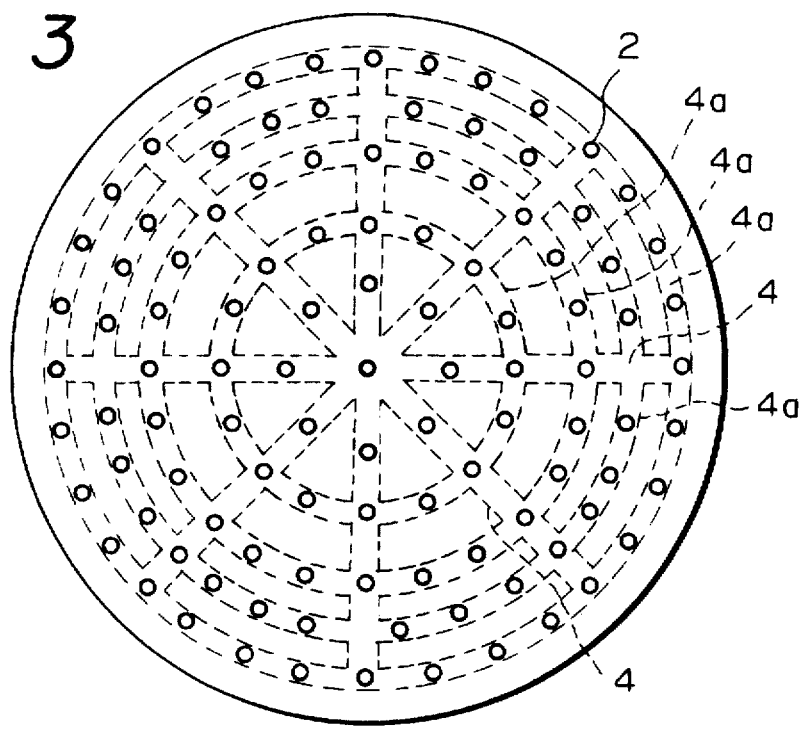
FIG. 3 is a plan view showing a specific pattern in which guide grooves and holes are arranged in a disk included in the embodiment.

FIG. 3 shows a specific pattern in which the guide grooves 4 and holes 2 are arranged in the disk 1. As shown, the radially extending guide grooves 4 are communicated to each other by concentric guide grooves 4a. The density of the concentric grooves 4a is sequentially increased toward the circumferential edge of the disk 1. The concentric grooves 4a are positioned at the intervals, e.g., 10 degrees at the central portion of the disk 1 and at the intervals of, e.g., 5 degrees at the peripheral portion, although not shown in FIG. 3 precisely. The holes 2 are formed in both the grooves 4 and the grooves 4a.

In the pattern shown in FIG. 3, the holes 2 are uniformly and densely arranged in the disk 1 and allow a great amount of effusion fluid to be collected at a time. Therefore, the area of the disk 1 can be further reduced for the same sampling amount.

Figure 4:
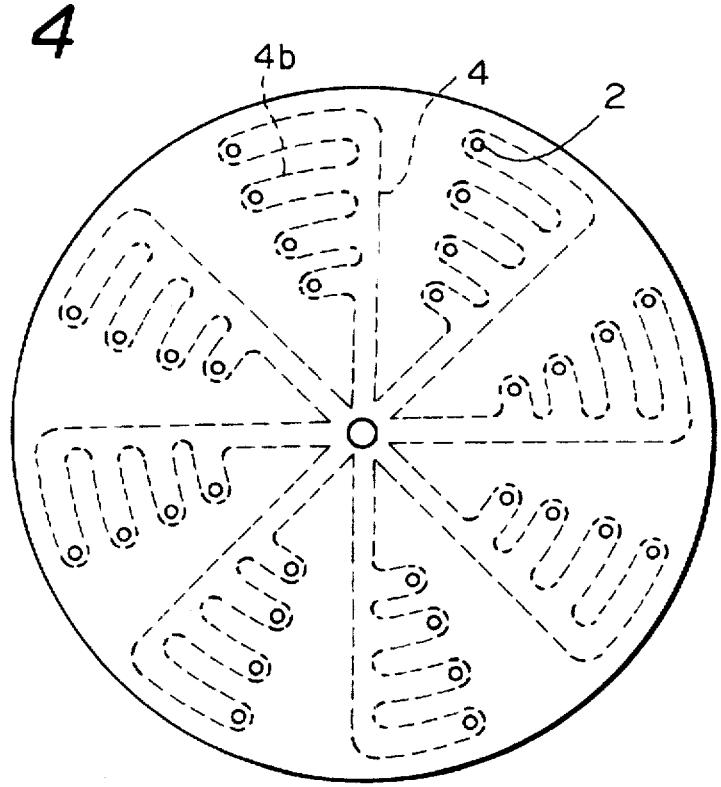
FIG. 4 shows another specific pattern of the guide grooves and holes.

FIG. 4 shows another specific pattern of the guide grooves 4 and holes 2. As shown, a plurality of second or auxiliary guide grooves 4b extend from each radial groove 4 in one direction in the circumferential direction of the disk 1.

The holes 2 are formed in the auxiliary grooves 4b. The auxiliary grooves 4b each has a width and a depth slightly smaller than those of the radial grooves 4. In this pattern, the radial grooves 4 should only serve to deliver the effusion fluid received from the holes 2 via the auxiliary grooves 4b toward the center of the disk 1. It follows that the flows of the fluid coming in various directions are prevented from colliding with each other or joining each other. This insures the smooth flow of the fluid toward the center of the disk 1 and thereby further enhances the sampling efficiency.

In any of the specific patterns shown in FIGS. 3 and 4, the surface of the disk 1 to contact the skin, except for the holes 2, may be formed with irregular grooves such that it has a surface roughness of several microns. Generally, the skin is extremely soft and deforms in such a manner as to stop the holes 2 in the event of evacuation. The above irregular grooves of the disk 1 will surely guide the fluid into the holes 2 despite the deformation of the skin.

Figure 5:
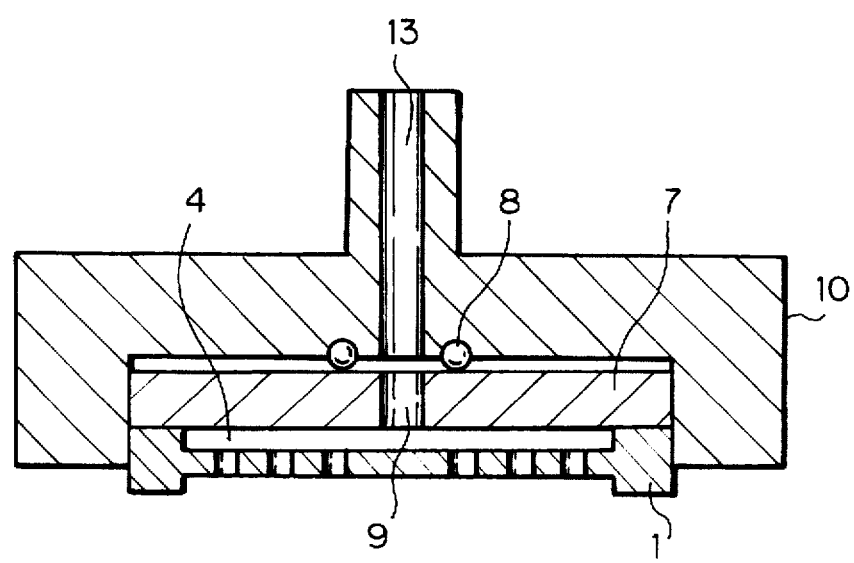
FIG. 5 is a section showing an alternative embodiment of the present invention.

Referring to FIG. 5, an alternative embodiment of the present invention will be described. In FIG. 5, the same or similar constituents as or to the constituents of the previous embodiment are designated by like reference numerals, and a detailed description thereof will not be made in order to avoid redundancy. As shown, an auxiliary disk 7 is disposed in the cavity of a suction cell 10 and closes the open ends of the guide grooves 4. A bore 9 is formed throughout the center of the auxiliary disk 7. An O-ring 8 is interposed between the auxiliary disk 7 and the wall of the cavity of the cell 10. The O-ring 8 prevents the effusion fluid from entering the gap between the cell 10 and the disk 7 and prevents air from leaking in the event of evacuation. The cell 10 is of the type lacking a collection chamber, so that the sucked fluid will be directly delivered to a sensor portion, not shown.

The second or auxiliary disk 7 is formed of the same material as the first or main disk 1. Assuming that the disk 1 is 0.1 mm thick, then the disk 7 is also provided with a thickness of 1 mm. The disk 7 is entirely bonded to the disk 1 in such a manner as to close all the guide grooves 4. The prerequisite with this embodiment is the bonding method which prevents the fine grooves 4 and holes 2 from being stopped up.

For example, assume that the disks 1 and 7 are implemented as thin sheets of metal. Then, after the disk 1 has been etched to form the grooves 4 and holes 2, the disks 1 and 7 are laid on each other. Then, the disks 1 and 7 are subjected to heat of about 950° C. and a pressure of about 3 k g/m m² in an environment not oxidizing metal. As a result, the disks 1 and 7 are bonded due to diffusion. Assume that the disks 1 and 7 are implemented as thin sheets of vinyl chloride or similar polymeric material. Then, the disk 1 is provided with fine lugs, not shown, in the form of trigonal pyramids between its guide grooves 4 by extrusion molding. Subsequently, the disks 1 and 7 are laid on each other, and then a vibrator emitting an ultrasonic wave is brought into contact with the disks 1 and 7. Although the disks 1 and 7 may be bonded by ordinary adhesive, applying adhesive without stopping the grooves 4 and holes 2 needs a number of extra steps.

This embodiment has the following advantage in addition to the advantages described in relation to the previous embodiment. The parts of the cell 10 and disk 7 adjoining each other and to be evacuated are isolated from the other parts by the O-ring 8; otherwise, the fluid is apt to turn round to the unnecessary parts and reduce the collection efficiency. Moreover, the turn-round of the fluid occurs little by little and obstructs accurate measurement. With the illustrative embodiment, it is possible to deliver the fluid to the suction port 13 with high efficiency.

In summary, it will be seen that the present invention provides an effusion fluid sucking device having various unprecedented advantages as enumerated below. (1) A first disk is received in the cavity of a cell for sucking an effusion fluid in contact with the surface of an organism. Guide grooves are formed in the surface of the disk facing a suction port while holes are formed through the disk in each guide groove. The disk allows a minimum of fluid to remain thereon and guides the fluid toward the suction side in order to enhance efficient collection. When the fluid is collected a plurality of times, the preceding fluid and the following fluid are prevented from being mixed together.. This enhances accurate measurement. (2) A second or auxiliary disk covers the open ends of the guide grooves and isolates the gap between the first disk and the cell from the suction side. This prevents the fluid from turning round to the above gap and thereby enhances efficient collection. In addition, no fluid is left on the disks, so that accurate measurement is further enhanced. (3) Because the first disk with the guide grooves a n d holes is produced by etching, it is feasible for quantity production and inexpensive. The first disk which is a single member sparingly deforms. An annular projection extending along the edge of the first disk insures tight contact between the disk and the skin, thereby obviating the leak of the fluid.

Various modifications will become possible for those skilled in the art after receiving the teachings of the present disclosure without departing from the scope thereof.

What is claimed is:

1. A device for sucking and collecting an effusion fluid from an organism, comprising:
    a suction cell comprising a suction port for causing the effusion fluid to effuse from the organism by evacuation, and a cavity formed in an end of said suction cell for directly contacting a surface of the organism;
    a first disk received in said cavity and for directly contacting the surface of the organism;
    wherein said first disk is formed with a plurality of guide grooves on a surface thereof facing said suction port, and a plurality of through holes in said plurality of guide grooves; and
    a second disk interposed between said first disk and said suction port, said second disk covering open ends of said plurality of grooves and formed with a through bore aligned with said suction port.

2. A device as claimed in claim 1, wherein said plurality of grooves extend radially on said first disk.

3. A device as claimed in claim 1, wherein said plurality of grooves comprise radially extending grooves and concentric grooves communicating said radially extending grooves to each other.

4. A device as claimed in claim 1, wherein said first disk further comprises an annular projection at an edge thereof for contacting the surface of the organism to thereby prevent vacuum from decreasing.

5. A device as claimed in claim 1, wherein the metal comprises stainless steel.

6. A device as claimed in claim 1, wherein said first disk has surfaces thereof formed of one of metal and resin sparingly ionizable against the effusion fluid.

7. A device as claimed in claim 6, wherein the metal comprises nickel.

8. A device as claimed in claim 6, wherein the resin comprises polyimide.

9. A device as claimed in claim 6, wherein the resin comprises vinyl chloride.

10. A device as claimed in claim 1, wherein said through holes and said guide grooves have a total capacity of about 10 μl.

11. A device for sucking and collecting a liquid effused from a surface of a multicellular organism comprising:
    a suction cell having a suction port;
    a cavity in an end of said suction cell, said cavity in communication with said suction port;
    a disk with at least one guide groove on a suction cell side of said disk, whereby said guide groove for guiding said liquid effused from said surface of said multicellular organism through at least a portion of said cavity;
    a plurality of through-holes through said disk, said through-holes providing communication between said suction cell side of said disk to an opposite side; and
    a cover disk on said suction cell side of said disk with at least one guide groove, said cover disk having a lumen in communication with said suction port said cover disk providing a cover on said at least one guide groove.

12. The device according to claim 11, wherein said disk has a thickness of about 0.1 mm.

13. The device according to claim 11, wherein said disk has a diameter of about 30 mm.

14. The device according to claim 11, wherein said at least one guide groove has a width of about 0.15 mm.

15. The device according to claim 11, wherein said at least one guide groove has a depth of about 0.05 mm.

16. The device according to claim 11, wherein said at least one guide groove has a length less than about 15 mm.

17. The device according to claim 11, wherein said at least one guide groove comprises a plurality of guide grooves in a radial pattern.

18. The device according to claim 11, wherein said at least one guide groove comprises at least one annular groove.

19. The device according to claim 11, wherein said through-holes have a diameter of about 0.1 mm.

20. The device according to claim 11, wherein said at least one guide groove is formed by etching.

21. The device according to claim 20, wherein said etching comprises photolithography.

22. The device according to claim 11, further comprising a biosensor for measuring a concentration of a chemical substance in said liquid effused.

23. The device according to claim 22, wherein said chemical substance is glucose.

24. The device according to claim 11, wherein said disk includes at least one annular projection on said opposite side.

25. The device according to claim 11, further comprising a collection chamber.

26. The device according to claim 11, further comprising an O-ring sealing between said suction port and said disk.

27. The device according to claim 11, further comprising an O-ring sealing between said suction port and said disk.

28. The device according to claim 11, wherein said disk comprises irregular grooves on said opposite side, said irregular grooves providing a surface roughness of several microns.

* * * * *